US006613756B2

(12) United States Patent
Duncan et al.

(10) Patent No.: US 6,613,756 B2
(45) Date of Patent: Sep. 2, 2003

(54) USE OF TETRACYCLINE DERIVATIVES IN TREATING MULTIPLE SCLEROSIS

(75) Inventors: Ian D. Duncan, Madison, WI (US); Su-Chun Zhang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/848,139

(22) Filed: May 3, 2001

(65) Prior Publication Data

US 2002/0022608 A1 Feb. 21, 2002

Related U.S. Application Data

(60) Provisional application No. 60/202,138, filed on May 5, 2000.

(51) Int. Cl.$^7$ ............................................... A61K 31/65
(52) U.S. Cl. ....................................... 514/152; 514/903
(58) Field of Search ................................. 514/152, 903

(56) References Cited

U.S. PATENT DOCUMENTS

| 5,789,395 A | 8/1998 | Amin et al. ................ 514/152 |
| 5,919,775 A | 7/1999 | Amin et al. ................ 514/152 |

FOREIGN PATENT DOCUMENTS

| WO | 00/64479 | 4/2000 |

OTHER PUBLICATIONS

WPIDS Accession No. 1996–444664, Opdenakker, EP 736302, Oct. 9, 1996, abstract.*

Benveniste, Etty N., Role of Macrophages/Microglia in Multiple Sclerosis and Experimental Allergic Encephalomyelitis, J. of Mol. Med. (1997) 75:165–173.

Duncan, Ian D., Transplant Strategies in Myelin Disorders, *Cell Transplantation for Neurological Disorders: Toward Reconstruction of the Human Central Nervous System*, Ed. T.B. Freeman and H. Widner, Humana Press, 1996.

Duncan, Ian D. et al., Repair of Myelin Disease: Strategies and Progress in Animal Modes, Mol. Med. Today, Dec. 1997, 554–561.

Saivin, S. et al., Clinical Pharmacokinetics if Doxycycline and Minocycline, Clin. Pharm. 15:356–357 (1988).

Selkoe, S. et al., Translating Cell Biology into Therapeutic Advances in Alzheimer's Disease, Nature v. 39, Jun. 24, 1999, A23–A31.

Sriram, S. et al., Indictment of the Microglia as the Villain in Multiple Sclerosis, Neurology 48: Feb. 1997, 464–470.

Yrjänheikki, Juha et al., Tetracyclines Inhibit Microglial Activation and are Neuroprotective in Global Brain Ischemia, Proc. Natl. Acad. Sci. USA: v.95, 15769–15774, Dec. 1998.

Yrjänheikki, Juha et al., A Tetracycline Derivative, Minocycline, Reduces Inflammation and Protects Against Focal Cerebral Ischemia with a Wide Therapeutic Window, PNAS, v.96,n.23, Nov. 9, 1999.

Goodman & Gilman's: *The Pharmacological Basis of, Therapeutics*, Ninth Edition, Chapter 47, 1124–1129, 1996.

\* cited by examiner

*Primary Examiner*—Rebecca Cook
(74) *Attorney, Agent, or Firm*—Quarles & Brady LLP

(57) ABSTRACT

A method of treating multiple sclerosis is disclosed. In one embodiment, the method comprises the step of treating a multiple sclerosis patient with a tetracycline derivative, wherein the multiple sclerosis symptoms of the patient are diminished.

15 Claims, 5 Drawing Sheets

USE OF TETRACYCLINE DERIVATIVES IN TREATING MULTIPLE SCLEROSIS

CROSS-REFERENCE TO RELATED APPLICATION

This application claims priority from U.S. provisional application No. 60/202,138, filed May 5, 2000. U.S. Ser. No. 60/202,138 is incorporated by reference herein.

STATEMENT REGARDING FEDERALLY SPONSORED RESEARCH OR DEVELOPMENT

BACKGROUND OF THE INVENTION

There is an urgent need for the development of new drugs or a new application of existing drugs to the treatment of multiple sclerosis and other incurable neurologic disorders. The application of tetracycline derivatives, such as minocycline or doxycycline, to the treatment of multiple sclerosis based on our data is an advance in the treatment of this disease, both as a primary therapy and in support of transplant-induced brain repair.

Multiple sclerosis is an inflammatory disease of the central nervous system (CNS) in which demyelination results in a variety of neurologic deficits. In many patients the disease relapses and remits while in others there is a progressive worsening with no remissions. At present, the only drugs that have been found to be effective in slowing or lessening the disease burden are β-interferon and copolymer-I. However, neither cures the disease and in many patients there is little or no effect. While T-cells are the early inflammatory cells found in areas of demyelination (plaques) in multiple sclerosis patients, microglia in these areas become activated and are thought to produce a number of cytotoxic cytokines. These cytokines are then thought to play a key role in the subsequent demyelination and oligodendrocyte death.

The best available model of multiple sclerosis is EAE (Experimental Allergic Encephalomyelitis). While there are differences between EAE and Multiple Sclerosis, EAE remains as the standard model in which to test therapeutic strategies. Indeed, some Phase I trials in multiple sclerosis patients have been based on experimental therapies of EAE. While EAE can be generated in both rats and mice and by using a number of protocols, we induce the disease in DA (Dark Agouti) rats by the injection of myelin-oligodendrocyte glycoprotein (MOG) in incomplete Freund's adjuvant. This creates a severe, often relapsing-remitting neurologic disease, like multiple sclerosis, with paralysis of the hind limbs 12–15 days after immunization. Histologically, there is scattered demyelination associated with inflammation and microglial activation.

BRIEF SUMMARY OF THE INVENTION

In one embodiment, the present invention is a method of treating multiple sclerosis comprising the step of treating a multiple sclerosis patient with a tetracycline derivative, wherein the derivative is lipid soluble, and wherein the multiple sclerosis symptoms of the patient are diminished.

In a preferred embodiment, the tetracycline derivative is selected from the group consisting of minocycline and doxycycline and the tetracycline derivative treatment is timed to prevent a relapse of multiple sclerosis symptoms.

In another embodiment of the invention, the treatment is at the time of a triggering event, typically a viral infection.

In another embodiment, the present invention is a method of treating multiple sclerosis patients wherein a multiple sclerosis patient is treated with a tetracycline derivative, wherein the tetracycline derivative is lipid soluble, prior to or at the same time as receiving a transplant of oligodendrocyte progenitor cells to repair chronic areas of the demyelination. Preferably, the tetracycline-derivative is supplied at least three days before transplantation of cells.

It is an object of the present invention to treat the symptoms of multiple sclerosis.

Other objects, features and advantages of the present invention will become apparent after one has examined the specification, claims and drawings.

BRIEF DESCRIPTION OF THE DRAWINGS

FIG. 1(A) demonstrates that the high-dose MOG immunization paradigm clinical course is significantly less severe (P<0.01) in rats treated with minocycline from day 1 post-immunization ($EAE^{tr}$, n=6), in comparison with PBS-treated rats ($EAE^{pbs}$, n=5). FIG. 1(B) demonstrates that the low-dose MOG immunization paradigm severity of EAE is significantly reduced (P<0.001) either when minocycline treatment starts before ($EAE^{tr1}$, n=6), or at the onset of disease with once ($EAE^{tr2}$, n=10), or twice ($EAE^{tr3}$, n=8) daily injections for the first two days, in comparison with $EAE^{pbs}$ (n=9). $EAE^{tr3}$ treatment is significantly more effective (P<0.01) in comparison with $EAE^{tr2}$. All data represent mean±SEM of clinical disease score.

(FIG. 5A): Treatment of high-dose MOG immunized rats with minocycline from post-immunization day 1 to 10 has no significant effect on the antigen specific proliferative response of cells isolated from the draining lymph nodes 10 d.p.i. (FIG. 5B): The humoral immune response after immunization with MOG is not dramatically attenuated by minocycline treatment from post-immunization day 1 to 10. Each bar represents the mean count per minute (c.p.m.)±SD (A) or mean absorbance±SD (B), both pooled from four donors assayed in quadruplicate.

DETAILED DESCRIPTION OF THE INVENTION

Figure 1:
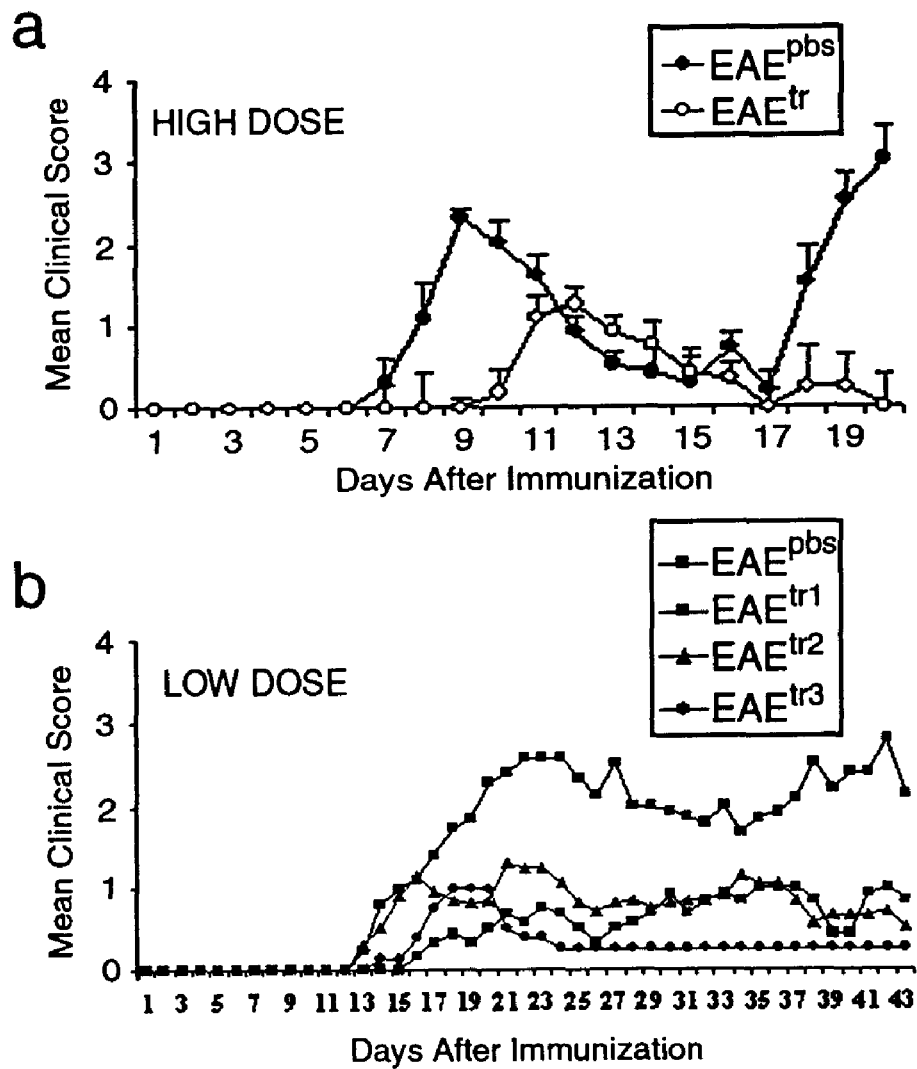
FIG. 1 shows that treatment with minocycline delays the onset and decreases clinical course of EAE.

While we have been exploring survival of oligodendrocytes transplanted into the spinal cords of these rats, we made initial discoveries in a mutant rat that led us to use the antibiotic minocycline in EAE. We have used the drug in a mutant rat known as Long Evans shaker (les) that has a severe, spontaneous microgliosis. Cells transplanted into these rats did not survive, and it was postulated that the activated microglial cells were responsible for their demise. At that time it had been reported that minocycline could prevent activation of microglia around stroke lesions in the gerbil brain (Yrjänheikki, et al., *Proc. Natl. Acad. Sci. USA* 95:15769–15774, 1998). This finding was subsequently confirmed showing that the drug had a wide therapeutic window and was neuroprotective (Yrjänheikki, et al., *Proc. Natl. Acad. Sci. USA* 96:13496–13500, 1999). We examined this drug to see whether a similar effect on microglia would be seen in the les rat and in animals with EAE.

Results of these experiments are described below in the Examples and in U.S. Provisional application No. 60/202,138 and describe the suppression of activated microglia by minocycline and the subsequent myelination of cells transplanted into the spinal cord at peak gliosis. Example 1 describes the prevention of disease development and lessening of the disease severity when MOG-immunized DA rats were treated with minocycline before onset of disease.

We propose that tetracycline derivatives, such as minocycline or doxycycline, be used to treat relapses in patients with multiple sclerosis. Appropriate tetracycline derivatives are lipid soluble semi-synthetic (second generation) compounds that have been modified from the original tetracycline formula. Yrjänheikki, et al., *Proc. Natl. Acad. Sci. USA* 96:[23]:13496–13500, 1999, describes the tetracycline derivative minocycline. *Goodman & Gilman's The Pharmacological Basis of Therapeutics Ninth Edition* McGraw Hill, New York, 1996, pp 1124–1129 describes the structure and function of tetracycline and common derivatives, including minocycline and doxycycline.

In addition there are a number of chemically modified tetracyclines (CMT's) numbered 1–5 (Rifkin, et al., *Anns. N.Y. Acad. Sci.* 7321:165–180, 1994) that have been synthesized to separate their anti-inflammatory properties from their antimicrobial actions. In particular, CMT-1 and CMT-3 have persistent anti-collagenase activity. This activity has been brought about by, for example, removal of the dimethylamino group from carbon-4 of the tetracycline molecule (i.e., CMT-1). CMT-1 is 4-dedimethylamino tetracycline and CMT-3 is 6-demethyl 6-deoxy 4-dedimethylamino tetracycline. Other CMT's in which the anti-inflammatory properties, such as MMP (metalloproteinase) inhibition are retained or enhanced would be candidate therapeutic agents based on our data.

Doxycycline and minocycline can be distinguished from the original tetracyclines by structural differences in positions 5 and 6 (doxycycline) and by substitution of a dimethylamino group in position 7 (minocycline). These substitutions cause few variations in the bacteriological properties, but do change the physiocochemical properties such as lipophilicity. Minocycline has a high partition coefficient (39.4). The partition coefficient of doxycycline is lower (0.63), although still higher than the partition coefficient of tetracycline (0.102). Tetracycline derivatives of the present invention will have a partition coefficient of greater than 0.102. Preferably, the partition coefficient is between 0.60 and 40.0.

The greater lipophilicity allows easier penetration of biological membranes, thus facilitating penetration into the body tissues.

Our present data suggest that the antibiotics can be used at dosages currently used in patients with rheumatoid arthritis at the time of onset of symptoms. (See Yrjänheikki, et al., supra) At this time, we predict that treatment will lessen the severity of symptoms, shorten the relapse, and help prevent persistent neurologic deficit. To prevent relapses from occurring with known triggering events such as viral infections (cold, flu), multiple sclerosis patients will be given minocycline or doxycycline prophylactically to completely block the occurrence of relapses.

A preferred treatment schedule is as follows: The treatment could be at time of relapse (first onset of clinical symptoms) or at the time of "triggering" events, such as an upper respiratory infection. A dose would typically be about 200 mg/day (±50 mg), but could be increased if the patient can tolerate it.

A typical dose would be oral. For prevention, treatment would preferably be 2–3 weeks. As a treatment, therapy would preferably be given 2–3 weeks or until full recovery. One would most typically look for diminished symptoms, such as improvement in muscle strength, lessening of fatigue symptoms, lessening of vision disturbances and lessening of abnormal sensory conditions. By "diminished," we mean the symptom is diminished by at least 50%. Preferably, the symptom is diminished by 90% or completely eradicated.

Tetracycline derivatives, such as minocycline (or doxycycline) will also be used in combination with cell therapy in multiple sclerosis patients who will receive transplants of cells to repair chronic areas of demyelination. We have shown that minocycline given three days before transplantation of cells in an animal model of multiple sclerosis can prevent the cells from dying. This approach would, therefore, also be used in multiple sclerosis patients who would be pre-treated with the drug to promote survival of the transplanted cells.

A typical treatment plan would be similar to that described above. Duncan, "Myelin Disorders" in *Cell Transplantation for Neurological Disorders: Toward Reconstruction of the Human Central Nervous System*, pp 287–302, Humana Press, and Duncan, et al., *Molecular Medicine Today*, December 1997, 554–561, describes standard cell treatment methods.

EXAMPLES

Multiple sclerosis (MS) is a chronic inflammatory demyelinating disease of the central nervous system (CNS), which classically follows a relapsing remitting course associated with an increasing neurological deficit. Currently, therapeutic strategies for MS target the immunological component of the disease and while beneficial, fail to prevent disease progression in many patients (Noseworthy, J. H., *Nature* 399(Suppl.):A40–A47, 1999). Demyelinated axons are highly susceptible to damage by free radicals and other inflammatory mediators (Pitt, D., et al., *Nature Med.* 6:67–70, 2000; Smith, T., et al., *Nature Med.* 6:62–66, 2000) which in MS leads to an irreversible loss of axons (Trapp, B. D., et al., *N. Engl. J. Med.* 338:278–285, 1998). Repeated episodes of inflammation and demyelination result in a progressive axonal loss of axons and a corresponding increase in chronic disability (Trapp, B. D., et al., supra, 1998; Van Waesberghe, J. H. T. M., et al., *Ann. Neurol.* 46:747–754, 1999; Kornek, B., et al., *Am. J. Pathol.* 157:267–276, 2000). There is, therefore, a vital need to explore alternative strategies that both limit inflammation in the CNS and promote axonal survival. These, along with strategies that promote remyelination, could be used in combined therapies that would address all aspects of MS pathology.

In the study reported below, we investigated minocycline, a second-generation tetracycline that exhibits pleiotropic anti-inflammatory and neuroprotective properties, as a treatment for experimental allergic encephalomyelitis (EAE), an animal model of MS. Minocycline is presently used to treat rheumatoid arthritis (Alarcon, G. S., *Rheum. Dis. Clin. North. Am.* 24:489–499, 1998; Greenwald, R. A., *Ann. NY Acad. Sci.*, pp. 181–198, 1994) and experimentally has been shown to modulate T-cell function (Kloppenburg, M., et al., *Clin. Exp. Immunol.*, pp. 635–641, 1995; Kloppenburg, M., et al., *Antimicrob. Agents Chemother.*, pp. 934–940, 1996). In addition it inhibits microglial activation, a key event in the immunopathogenesis of MS, (Benveniste, E. N., *J. Mol. Med.* 75:165–173, 1997; Gonzalez-Scarano, F. and Baltuch, G., *Annu. Rev. Neurosci.* 22:219–240, 1999) in experimental models of focal and global ischemia (Yrjänheikki, J., et al., *Proc. Natl. Acad. Sci. USA* 95:15769–15774, 1998; Yrjänheikki, J., et al., *Proc. Natl. Acad. Sci. USA* 96:13496–13500, 1999). More recently, minocycline has also been shown to be neuroprotective. In vitro, it promotes survival of cultured neurons when exposed to glutamate, (Yrjänheikki, J., et al., supra, 1999) and also delays disease progression in a transgenic mouse model of Huntington's disease, an effect associated with the inhibition of caspases 1 and 3, and iNOS (Chen, M., et al., *Nature Med.* 6:797–801, 2000).

We report herein that minocycline dramatically suppresses disease activity in chronic relapsing remitting EAE induced by the myelin oligodendrocyte glycoprotein (MOG), an animal model that reproduces the clinical course and immunopathology of MS (Storch, M. K., et al., *Brain Pathol.* 8:681–694, 1998; Raine, C. S., et al., *Ann. Neurol.* 46:144–160, 1999). Crucially, minocycline suppresses clinical disease and histopathological evidence of inflammation, demyelination, and axonal death when given therapeutically after disease onset. Mechanistically, the therapeutic effect of minocycline is not due to suppression of the MOG-specific response in the periphery, but rather due to its pleiotropic effects that disrupt the inflammatory process within the CNS.

Results

Minocycline suppresses disease activity in EAE

Immunization with 100 $\mu$g MOG results in a severe, biphasic disease that is normally lethal within 20 to 30 days, whereas reducing the dose of antigen to 10–25 $\mu$g induces a relapsing remitting disease course with low mortality (Table 1, below). In the high dose paradigm, daily-prophylactic treatment with minocycline starting from the day after immunization had a dramatic effect on disease activity. Disease onset was delayed and its severity dramatically reduced, such that all animals were healthy by 20 d.p.i., whereas the PBS-treated controls were in relapse with severe clinical disease (P<0.01) (FIG. 1A, Table 1).

The marked prophylactic effect of minocycline on this lethal model of EAE led us to investigate its therapeutic potential in relapsing remitting disease induced using 10 $\mu$g MOG, a paradigm that more closely replicates the chronic clinical course of MS (Chen, M., et al., supra, 2000). We observed that minocycline treatment significantly suppressed disease activity (P<0.001) even if treatment was only started two to three days before the expected onset of disease. In comparison to the sham-treated controls, minocycline markedly suppressed the severity of both the initial phase of disease and duration of subsequent relapses (see $EAE^{rr1}$ in FIG. 1B and Table 1).

Therapeutic treatment with minocycline abolishes disease activity

The observation that minocycline had a significant impact on disease activity even when treatment was delayed, suggested that this drug could also be used to suppress established clinical disease. We therefore delayed treatment with minocycline until the rats developed clinical grade 1 disease. We observed that within two to three days of starting the treatment, the neurological deficit stabilized and the mean maximal clinical score was significantly reduced in comparison to the MOG-immunized, sham-treated controls (P<0.001) (Table 1). Moreover, there was no further disease progression throughout the remainder of the study period (see EAE$^{tr2}$, FIG. 1B).

In order to improve the clinical outcome of therapeutic minocycline treatment we investigated the effect of doubling the dose during the period immediately after disease onset. Animals were treated twice daily for the first two days following the onset of EAE and thereafter once a day for the remainder of the study period (see EAE$^{tr3}$, FIG. 1B). This protocol effectively blocked the development of any chronic neurological deficit. None of the animals progressed beyond grade 1 disease, which in most cases resolved completely with no subsequent episodes of disease. Initial treatment with high dose minocycline at disease onset therefore produced a significant improvement in clinical outcome compared to a regime of single daily injections of minocycline throughout the treatment period (P<0.01) (FIG. 1B and Table 1). Treatment of naive, non-immunized animals with minocycline was not found to induce any adverse effects.

Minocycline reduces CNS pathology in MOG-induced EAE

Clinical disease in sham-treated rats with MOG-EAE was associated with the formation of large, confluent inflammatory demyelinating lesions scattered throughout the CNS with preferential localization in the thoracic-lumbar region of the spinal cord, in particular the dorsal funiculus. These subpial and perivascular lesions were characterized by large accumulations of infiltrating lymphocytes and macrophages, myelin loss, and axonal degeneration (FIG. 2).

Figure 2:
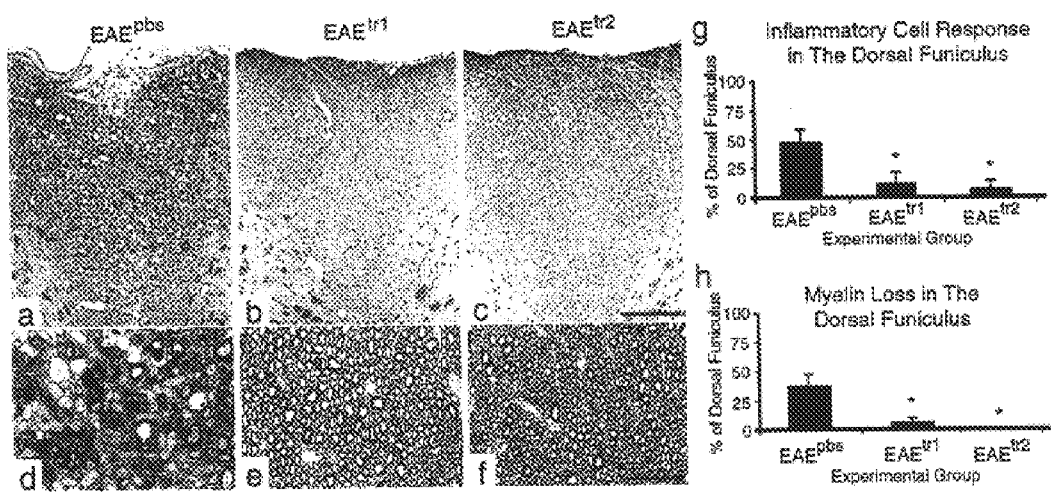
FIG. 2 shows that minocycline treatment markedly attenuates histological severity of EAE. Hematoxylin and eosin staining (FIGS. 2A–C, G) and toluidine blue stained thin sections (FIGS. 2D–F, H) reveal extensive inflammatory infiltrates (FIG. 2A) and confluent demyelination (FIG. 2D) in the dorsal funiculus of the spinal cord of the low-dose MOG immunized PBS-treated rats ($EAE^{pbs}$, n=10). In contrast, absence of signs (FIGS. 2B, E) or very mild signs (FIGS. 2C, F) of inflammation and demyelination are found in rats treated with minocycline before ($EAE^{tr1}$, n=10) or at the onset of disease ($EAE^{tr2}$, n=5), respectively. Bars represent mean±SEM of the histopathological score for the dorsal funiculus of the spinal cord. Statistical significance was determined using the Student's t-test (*P<0.05 and **P<0.01). Scale bar represents 800 µm (FIGS. 2A–C) or 40 µm (FIGS. 2D–F).

Treatment with minocycline significantly reduced CNS pathology irrespective of whether treatment was initiated before or at the onset of clinical disease (FIG. 2). Lesions in minocycline-treated groups were less frequent, usually located only in single segments of spinal cord, and markedly smaller in comparison with those seen in the sham-treated controls. These observations were confirmed by quantitative analysis of inflammation and demyelination in the dorsal funiculus of the spinal cord that revealed that the clinical effect of minocycline was accompanied by a dramatic reduction in both inflammation and demyelination (FIGS. 2G and H). A similar difference between minocycline-treated and sham-treated animals was seen in the high dose animals (data not shown).

Figure 3:
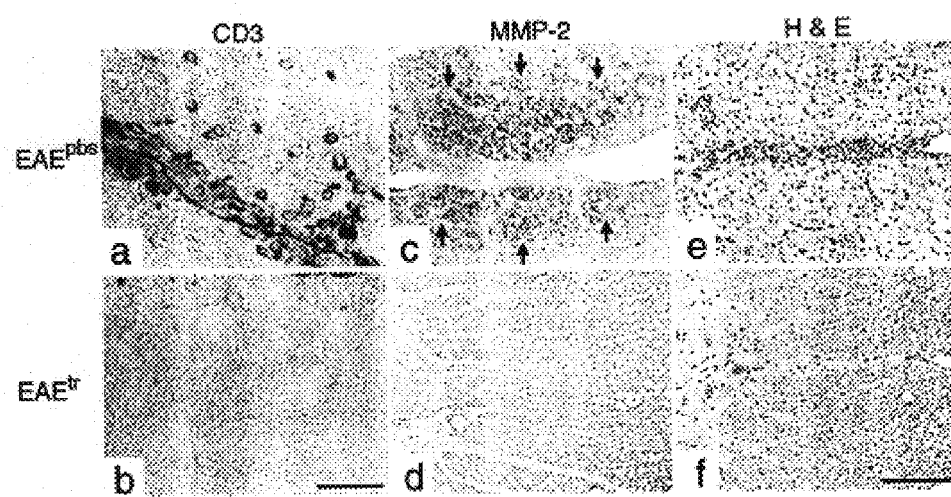
FIG. 3 shows that minocycline treatment suppresses infiltration of macrophages and microglial activation in the CNS. Immunohistochemical staining for CR3 (FIGS. 3A–D) and MHC II (FIGS. 3E–H) expression shows activated microglia/macrophages in the spinal cord of low-dose MOG immunized, PBS-treated rats ($EAE^{pbs}$, n=10) (FIGS. 3A, E). In contrast, animals treated with minocycline before ($EAE^{tr1}$, n=10) (FIGS. 3B, F), or at the onset of disease ($EAE^{tr2}$, n=5) (FIGS. 3C, G), reveal resting microglia, similar to naive ($N^{pbs}$, n=5) (FIGS. 3D, H) and minocycline treated naive animals ($N^{tr1}$, n=5) (data not shown). Treatment $EAE^{tr1}$ is more effective than $EAE^{tr2}$ in attenuating macrophage infiltration and microglia activation (FIGS. 3I, J). Bars represent mean±SEM of the histopathological score for the dorsal funiculus of the spinal cord. Statistical significance was determined using the Student's t-test (*P<0.05, ** P<0.01). Scale bar represents 200 µm.

This reduced inflammatory response in the CNS was accompanied by a marked decrease in the local expression of CR3 and MHC II. In sham-treated rats with EAE, large numbers of CR3$^+$, MHC II$^+$ rounded, activated microglia/macrophages were observed in the spinal cord. In contrast in animals treated with minocycline either before or at the onset of disease, we observed that these rounded, activated cells were absent and only "resting" class II$^+$ microglia with long branched processes were present. In animals treated at the onset of disease these MHC II expressing cells were usually diffusely distributed through the whole dorsal funiculus, whereas in animals treated with minocycline before the onset of disease these cells occurred as small, distinct accumulations (FIG. 3). These observations were confirmed by semi-quantitative analysis of immuno-positive cells in the dorsal funiculus. The levels of both CR3 and MHC class II specific staining were significantly reduced in both EAE$^{tr1}$ and EAE$^{tr2}$ minocycline treatment paradigms, although expression was still elevated relative to normal healthy naive animals (groups N$^{pbs}$ and N$^{tr1}$, FIGS. 3I and J) indicating some degree of residual pathology in the CNS (FIGS. 3I and J). A similar effect on MHC class II expression was also seen in rats receiving the high dose of MOG.

Figure 4:
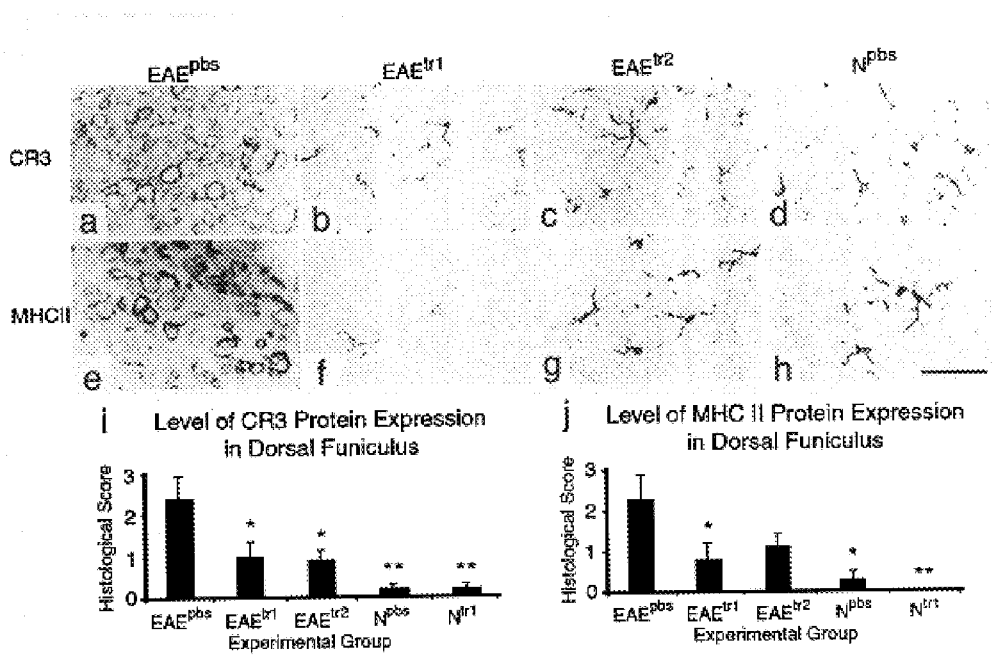
FIG. 4 shows that minocycline treatment diminishes T-cell infiltration/inflammation and MMP-2 expression in the spinal cord of high dose MOG-immunized rats. Large infiltrates of T-cells are observed in PBS-treated animals (EAE$^{pbs}$) ten days after immunization (FIG. 4A) in contrast to their absence in minocycline-treated animals (EAE$^{tr}$) (FIG. 4B). Serial sections from PBS-treated and minocycline-treated animals immunolabelled for MMP-2 (FIGS. 4C, D) and stained with hematoxylin and eosin (FIGS. 4E, F) reveal co-localization of MMP-2 protein and inflammatory infiltrates in PBS-treated (FIGS. 4C, E) in contrast to minocycline-treated animals (FIGS. 4D, F) twenty days after immunization. Scale bar represents 150 µm (FIGS. 4A, B) or 800 µm (FIGS. 4C–F).

Minocycline had a similar effect on the T-cell infiltrate within the CNS. Analysis of the spinal cord of rats 10 d.p.i. after immunization with 100 μg MOG revealed the presence of many focal T-cell infiltrates, as well as 3 scattered T-cells throughout the parenchyma of the cervical spinal cord of all sham-treated animals (FIG. 4A). In contrast, in animals treated with minocycline the number of T-cells invading the CNS was dramatically reduced (FIG. 4B). In a sample of three animals, focal T-cell infiltrates were only observed in the dorsal column of the cervical cord of one of three animals, while only scattered, subpial T-cells were detected in the spinal cords of the remaining two animals. Immunolabeling for MMP-2 revealed that MMP expression was up-regulated in areas of inflammation in the sham-treated rats (FIG. 4C) and was absent in those rats treated with minocycline (FIG. 4D).

Figure 5:
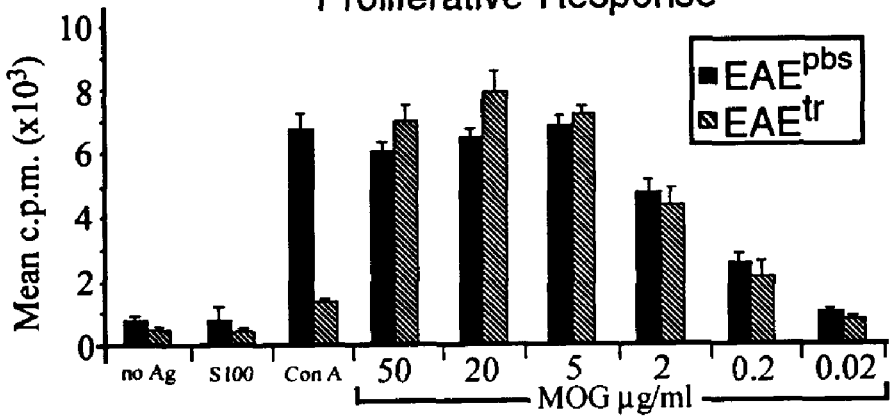
FIG. 5 shows that MOG-specific proliferative T-cell and serum IgG response is not affected by minocycline treatment.
Figure 5:
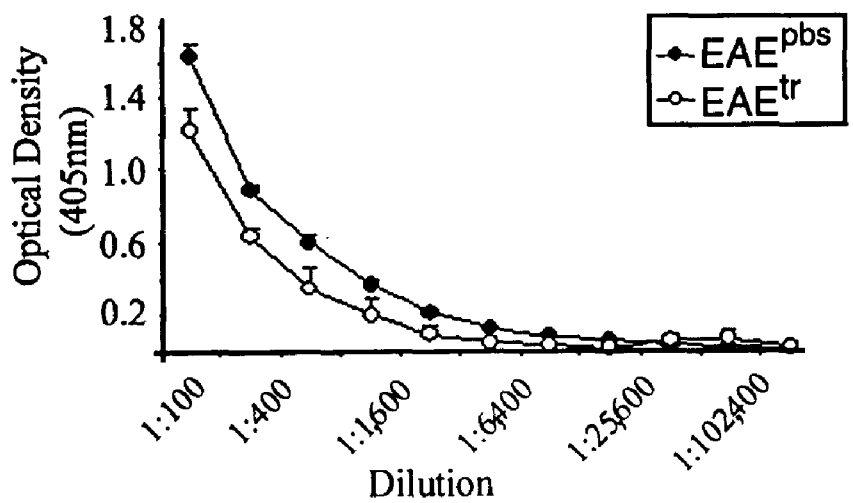

Minocycline does not act by suppressing the antigen specific response in the periphery Our histopathological results clearly demonstrate that minocycline suppresses inflammation within the CNS of animals with MOG-EAE. In view of the published data on the immunosuppressive potential of minocycline we speculated that its clinical efficacy in EAE was due to inhibition of the MOG-specific immune response. We therefore investigated its effect on the induction of the MOG-specific autoimmune response in animals immunized with 100 μg MOG and then treated daily with minocycline (FIG. 1A). Strikingly, we failed to detect any significant effect on either the MOG-specific T-cell or antibody response that could account for the striking clinical effect of this drug. Analysis of lymph node cells taken 10 d.p.i. revealed that minocycline did not suppress the antigen specific T-cell response as judged by either proliferation (FIG. 5A), or the synthesis of IFN-y and IL-10 (data not presented). Similarly, ELISA also failed to demonstrate any dramatic effect on the MOG-specific antibody response, although we did observe a slight reduction in the treated animals (FIG. 5B). These results indicate that minocycline does not simply act as an immunosuppressive agent, by inhibiting the induction of effector T and B cell responses in this model of MS, but rather more specifically by suppressing the ability of these effector mechanisms to initiate an inflammatory response within the CNS.

Discussion

It is also apparent from our data that T-cell recruitment into the CNS is also suppressed although not entirely eliminated in the treated animals. This effect may be mediated via the down-regulation of metalloproteinase (MMP) activity by minocycline, a mechanism previously postulated to be effective in EAE therapy (Liedtke, W., et al., *Ann. Neurol.* 44:35–46, 1998; Kieseier, B. C., et al., *Neurology* July (1 of 2):20–25, 1999). MMPs are crucially involved at many stages of the immunopathogenesis of EAE, in particular degradation of BBB function, leucocyte recruitment, and the release of pro-inflammatory cytokines. In this study we demonstrate that MMP-2 expression is increased in areas of inflammation in sham-treated rats with EAE, a response that is completely abrogated in animals treated with minocycline, even in areas with evidence of a local T-cell infiltrate. Intriguingly alpha-4 integrin mediated induction of MMP-2 expression plays a crucial role in the pathogenesis of EAE, (Graesser, D., et al., *J. Neuroimmunol.* 109:121–131, 2000) degrading the subendothelial basement membrane and facilitating T-cell/macrophage entry into the CNS. Disruption of the coordinate activation of MMP-2 may also influence the subsequent expression of other MMPs, such as MMP-9, which also plays a vital role in EAE and MS (Yong, V. W., et al., *Trends Neurosci.,* pp. 75–80, 1998). MMP 9 has been shown in vitro to play an important role in T-cell migration and this can be inhibited by IFβ1 (Leppert, D., et al., *Ann. Neurol.* 40:846–852, 1996; Stüve, O., et al., *Ann. Neurol.* 40:853–863, 1996). Experimental data from models of rheumatoid arthritis support this view that inhibition of MMP expression is at least in part responsible for the clinical efficacy of minocycline (Greenwald, R. A., et al., *J. Rheumatol.,* pp. 927–938, 1992). Not only are MMPs involved in disease pathogenesis, but tetracycline therapy actually suppresses MMP production.

Apart from these effects on the BBB and T-cell mediated induction of the local inflammatory response, we also present clear evidence that microglial activation is also decreased in EAE following minocycline treatment. Currently it is unclear whether this is due to a direct effect of minocycline, as described in experimental ischemia, (Yrjänheikki, J., et al., supra, 1998; Yrjänheikki, J., et al., supra, 1999) or is secondary to the general inhibition of CNS inflammation, or a combination of both. Intriguingly, we find that minocycline treatment is protective in a neural transplant paradigm in which microglial activation results in death of the transplanted cells (Zhang, unpublished observations), an observation suggesting that the drug may block the production of cytotoxic mediators associated with microglial activation. In established MS this effect may prove very important therapeutically by reducing the local production of pro-inflammatory mediators such as free radicals which would otherwise damage demyelinated axons in the lesion.

In addition to blocking or reducing inflammation and immune mediated damage per se, minocycline treatment may also be neuroprotective and reduce axonal damage directly. Minocycline has been shown to exert neuroprotective properties in two models. In vitro, glutamate-induced death of cultured sensory neurons was prevented by the addition of minocycline to the culture media, (Yrjänheikki, J., et al., supra, 1999) and minocycline therapy in vivo prolonged survival in a transgenic model of Huntington's disease, possibly due to the inhibition of caspase 1 and 3 (Li, M., et al., *Science* 288:335–283, 2000). This is especially relevant to the therapy of MS in light of the recent proliferation of literature that suggests that axonal death may be the key to long term disability in this disease (Trapp, B. D., et al., supra, 1998).

As a drug commonly used as an antibiotic in clinical practice, and in the therapy of the autoimmune disease rheumatoid arthritis, minocycline would thus seem to be an ideal candidate for a clinical trial in MS. While its efficacy might be greatest if given prior to the onset of clinical signs, for example at a time when a triggering episode such as a viral infection occurs, our data suggest that it could be given at relapse onset. Its intermittent use may have advantages over the β-interferon drugs, which need to be given for life; but long term treatment with minocycline is also possible (as is currently the case in the treatment of acne (Goulden, V., et al., *Br. J. Dermatol.* 693–695, 1996)) and could extend its use into patients with other forms of MS. It is not yet proven that long term therapy with β-interferon will result in axonal protection and the possibility that minocycline may also be a useful neuroprotective drug suggests that minocycline could become a therapy of choice in MS. Additionally, minocycline would be a much less expensive therapy than those currently approved for the treatment of MS. In addition, minocycline could be used in other demyelinating disorders such as adrenoleucodystrophy (Powers, J. M. and Moser, H. W., *Brain Patho.* 8:101–120, 1998) and the Guillain-Barré syndrome, (Griffin, J. W., et al., *Ann. Neurol.* 27(Suppl):S64–S68, 1990) where T-cell recruitment and inflammation also play a key role in their pathogenesis.

Methods

Experimental animals and antigens

Experiments were performed on 6–8 week old female DA rats obtained from Harlan-Sprague Dawley, Indianapolis, Ind. or Harlan-Winkelmann, Germany. During the observation period, rats were housed in a light- and temperature-controlled environment and were permitted free access to food and water. The recombinant extracellular immunogobulin domain of MOG was expressed in *E. coli* and purified as described previously (Raine, C. S., et al., *Ann. Neurol.* 46:144–160, 1999).

Immunization protocols

Rats were immunized sub-cutaneously (s.c.) at the base of the tail with either 10 $\mu$g MOG in complete Freund's adjuvant (CFA) or 100 $\mu$g MOG emulsified in incomplete Freund's adjuvant (IFA) (Difco, Detroit, Mich.) in a total volume of 100 $\mu$l. Animals were weighed and examined daily for clinical signs of EAE that was scored on the following scale: 0.5, partial loss of tail tone; 1, complete tail atony; 2, hind limb weakness; 3, hind limb paralysis; 4, moribund; 5, dead.

Minocycline treatment

Minocycline hydrochloride (Sigma, St. Louis, USA) was freshly dissolved in distillate water and administered daily by intraperitoneal (i.p.) injections at a dosage of 45 mg/kg rat body weight. In the high-dose MOG immunization paradigm rats were separated into two groups: $EAE^{pbs}$-phosphate-buffered saline (PBS)-treated rats (n=5) from day 1 post-immunization and $EAE^{tr}$-minocycline-treated rats (n=6) from day 1 post-immunization.

In the low-dose MOG immunization paradigm rats were separated into four groups according to minocycline treatment regimen: $EAE^{pbs}$-PBS-treated from the first clinical signs of EAE (n=15), $EAE^{tr1}$-minocycline-treated from post-immunization day 10 (n=15); $EAE^{tr2}$-minocycline-treated from the onset of EAE (n=10), and $EAE^{tr3}$-minocycline-treated from the onset of EAE with twice daily injections during the first two days followed by single injection throughout the remaining treatment period (n=8). Matched unimmunized, naive groups were also included:

$N^{pbs}$-PBS-treated animals (n=10), $N^{tr1}$-minocycline-treated from experimental day 10 (n=10), $N^{tr2}$-minocycline-treated from experimental day 13 (n=5), $N^{tr3}$ minocycline-treated from experimental day 13, with twice daily injections during the first two days followed by single injection throughout the remaining treatment period (n=5).

Neuropathological evaluations

Animals were deeply anesthetized with pentobarbital and perfused transcardially with Ringer's followed by 4% paraformaldehyde. The brain and spinal cord were removed and prepared for paraffin and epon embedding or cryo-protected in 30% sucrose. Paraffin sections were used to assess the degree of inflammation (hematoxylin and eosin) and one-micron semithin sections were used to estimate the demyelination in the spinal cord (toluidine blue). Areas with inflammatory infiltrates or demyelinating lesions in the dorsal funiculus of spinal cord were scored using a CCD72 camera to collect digital images that were analyzed with the Microcomputer Imaging Device (MCID) software from Imaging Research Inc. (St. Catherines, Ontario). Measurements for cell infiltrates and demyelination were expressed as percent of the total white matter area of the dorsal funiculus. To determine the profile of inflammatory infiltrates within lesions 10 $\mu$m cryostat sections of thoracic-lumbar spinal cord were immunolabelled for MHC II (Harlan Sera-Lab), CR3, CD45 (Serotec), GFAP (Dako), CD3 (PharMingen) and MMP-2 (Oncogne Research Products) protein expression. Primary antibodies were detected using a biotinylated secondary antibodies and the avidin: biotin enzyme complex technique (Vector Laboratories). Areas with immunolabelling-defined inflammatory infiltrates were scored using a semi-quantitative scale: 0-no inflammatory infiltrates or lesions, 1–25%, 2–50%, 3–75%, and 4–100% of the dorsal funiculus.

Immunological investigations

Draining lymph nodes and spleens were removed 10 days post-immunization (d.p.i.) and proliferation assays performed in flat-bottomed 96-well tissue culture plates in a total volume of 200 $\mu$l using either $5 \times 10^5$ lymph node or spleen cells (Raine, C. S., et al., supra, 1999). Antigen specific proliferation was assessed by the incorporation of $^3$H-thymidine (10 $\mu$Ci/well) during the final 18 hours of a 72 hour culture period using a Packard Matrix 96 Direct Beta counter.

Blood was collected immediately before perfusion and the sera stored at $-20°$ C. ELISA was performed using polystyrene 96-well PVC plates (Costar, Cambridge, U.S.A.) coated overnight at 4° C. with 10 $\mu$g/ml antigen in phosphate-buffered saline (PBS) (pH 7.4) containing 0.02% $NaN_3$. The plates were washed with PBS/0.02% $NaN_3$ containing 0.05% Tween 20 (Sigma, FRG) and blocked with 1% BSA in PBS containing 0.02% $NaN_3$ (pH 7.4) overnight at 4° C. After washing with PBS-Tween, 100 $\mu$l of serial serum dilutions in PBS were incubated for one hour at 37° C. Anti-MOG IgG antibody levels were determined directly using 100 $\mu$l of alkaline phosphatase-conjugated rat IgG specific goat antibody (1:2000). All plates were developed with p-nitrophenyl phosphate (Sigma, FRG) in 1 M diethanolamine, 0.02% $NaN_3$, 4 mM $MgCl_2$, pH 9.8 and optical density determined at 450 nm.

Statistical analysis

Statistical analysis of clinical scores was performed by averaging them over all times of the treatment and subtracting the first 11 days after immunization when clinical score in all groups was 0. Statistical significance was established using a repeated measures analysis where clinical score between treatments was compared from day 12 to 42 building in an auto-correlation of the error term. ANOVA and Student's t-test were used to establish the difference between experimental groups in all other examined parameters. Statistically significant differences were presented as: * for $P<0.05$,  for $P<0.01$, and * for $P<0.001$.

TABLE 1

Changes in Clinical and Neuropathological Course of EAE After Treatment with Minocycline

| EAE Paradigm | Treatment | n | % Of Incidence | % Of Mortality | Mean Cumulative Score | % Of Dorsal Column Demyelinated |
|---|---|---|---|---|---|---|
| 100 $\mu$g rMOG/IFA | PBS from day 1 | 5 | 100 | 100 | 17.3 | 66.5 |
| | Minocycline from day 1 | 6 | 80 | 0 | 5.5 | 6.25 |
| 10 $\mu$g rMOG/CFA | PBS from day of onset | 15 | 80 | 16.66 | 54.11 | 37.71 |
| | Minocycline from day 10 | 15 | 40 | 0 | 7.43 | 5.94 |
| | Minocycline from day of onset | 10 | 100 | 0 | 26.25 | 0.12 |
| | Minocycline from day of onset (Double-dose) | 8 | 100 | 0 | 10.12 | 0.04 |

Table 1 demonstrates that minocycline therapy suppresses disease activity and reduces CNS pathology in MOG-immunized rats. Cumulative score is the sum of all daily scores of all animals divided by the number of animals. The high-dose MOG immunization paradigm experiment was terminated on day 20 due to the severity of disease in PBS-treated animals. Rats treated with PBS in the low-dose MOG immunization paradigm were sacrificed either when the severity of disease reached clinical score 4 or 42 days after immunization when clinical scores ranged from 1 to 3. Minocycline treated rats from the low-dose immunization paradigm were sacrificed 42 days after immunization.

We claim:

1. A method of treating the symptoms of multiple sclerosis in a patient in need thereof comprising administering to said patient an effective amount of a lipid soluble tetracycline derivative.

2. The method of claim 1 wherein the tetracycline derivative is selected from the group consisting of minocycline and doxycycline.

3. The method of claim 1 wherein the tetracycline derivative treatment is timed to prevent a relapse of multiple sclerosis symptoms.

4. The method of claim 1 wherein the dose of tetracycline derivative is 200 mg/day (±50 mg).

5. The method of claim 1 wherein treatment duration is between 2 and 3 weeks.

6. The method of claim 1 wherein treatment is until cessation of symptoms.

7. The method of claim 3 wherein the treatment is at the time of a triggering event.

8. The method of claim 7 wherein the triggering event is a viral infection.

9. A method of treating a patient having multiple sclerosis prior to or at the same time as receiving a transplant of oligodendrocyte progenitor cells to repair chronic areas of demyelination comprising administering to said patient an effective amount of a lipid soluble tetracycline derivative prior to or at the same time as receiving said transplant.

10. The method of claim 9 wherein the tetracycline-derivative is supplied at least three days before transplantation of cells.

11. The method of claim 9 wherein the tetracycline derivative is selected from the group consisting of minocycline and doxycycline.

12. The method of claim 1 wherein the lipid soluble tetracycline derivative is minocycline.

13. The method of claim 1 wherein the tetracycline derivative is doxycycline.

14. The method of claim 9 wherein the tetracycline derivative is minocycline.

15. The method of claim 9 wherein the tetracycline derivative is doxycycline.

* * * * *